(12) United States Patent
Cohen

(10) Patent No.: US 7,597,914 B1
(45) Date of Patent: Oct. 6, 2009

(54) ALA-SEPTIC PRE-CANCEROUS LIQUID DISSOLVING SOLUTION AND METHOD

(76) Inventor: Allen Jay Cohen, 4626 Mirabella Ct., St. Pete Beach, FL (US) 33706

( * ) Notice: Subject to any disclaimer, the term of this patent is extended or adjusted under 35 U.S.C. 154(b) by 0 days.

(21) Appl. No.: 12/286,258

(22) Filed: Sep. 29, 2008

Related U.S. Application Data

(60) Provisional application No. 60/977,060, filed on Oct. 2, 2007.

(51) Int. Cl.
*A61K 36/886* (2006.01)
(52) U.S. Cl. .................. 424/744; 514/179; 514/458
(58) Field of Classification Search ........................ None
See application file for complete search history.

(56) References Cited

U.S. PATENT DOCUMENTS 4,880,637 A * 11/1989 Jordan ........................ 424/641
5,604,258 A * 2/1997 Ferrante et al. ............. 514/560
6,387,382 B1 * 5/2002 Saleh et al. .................. 424/401
2003/0017122 A1 * 1/2003 Vromen ........................ 424/59
2003/0129208 A1 * 7/2003 Alberts et al. ............... 424/400
2003/0207818 A1 * 11/2003 Jia et al. ....................... 514/27
2005/0049202 A1 * 3/2005 Kastelic et al. ............... 514/19
2005/0064025 A1 * 3/2005 Litchenberger et al. ..... 424/450

OTHER PUBLICATIONS

Kamb (Nature Reviews: Drug Discovery (2005), vol. 4, pp. 161-165).*
http://plants.usda.gov/java/profile?symbol=LATRT—accessed Mar. 2009.*

* cited by examiner

*Primary Examiner*—Susan C Hoffman

(57) ABSTRACT

Alcohol constitutes a majority of the solution. Water, melaleuca alternifolia, amebicidal, acetate, aloe barbadensis, larrea tridentat and benzoic acid constitute a minority of the solution. The minority of the solution optionally includes a corticosteroid and a nutritional supplement.

1 Claim, No Drawings

ALA-SEPTIC PRE-CANCEROUS LIQUID DISSOLVING SOLUTION AND METHOD

RELATED APPLICATION

The present non-provisional U.S. Patent Application is based upon U.S. Provisional Application No. 60/977,060, filed Oct. 2, 2007, the subject matter of which is incorporated herein by reference.

BACKGROUND OF THE INVENTION

Field of the Invention

The present invention relates to an ala-septic pre-cancerous liquid dissolving solution and method and more particularly pertains to dissolving pre-cancerous tumors and lesions of the skin.

SUMMARY OF THE INVENTION

In view of the disadvantages inherent in the known types of medicinal solutions of known designs and configurations now present in the prior art, the present invention provides an improved ala-septic pre-cancerous liquid dissolving solution and method. As such, the general purpose of the present invention, which will be described subsequently in greater detail, is to provide a new and improved ala-septic pre-cancerous liquid dissolving solution and method which has all the advantages of the prior art and none of the disadvantages.

To attain this, the present invention essentially comprises an ala-septic pre-cancerous liquid dissolving solution and method. First provided is a solution. The solution is a topical medication. The solution is comprised of anti-bacterial, anti-fungal and anti-viral elements. In this manner pre-cancerous tumors and lesions of the skin are dissolved. The specific solution, in the preferred embodiment, contains 60 percent ethyl alcohol, 11 percent purified water, 10 percent melaleuca alternifolia, 5 percent hydrocortisone, 5 percent iodoquinol, 2 percent tocopheryl acetate, 2 percent aloe barbadensis, 2 percent larrea tridentat, 2 percent oat flour isopropyl palmitate, and 1 percent benzoic acid.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved ala-septic pre-cancerous liquid dissolving solution and method which has all of the advantages of the prior art solutions of known designs and configurations and none of the disadvantages.

It is another object of the present invention to provide a new and improved ala-septic pre-cancerous liquid dissolving solution which may be easily and efficiently manufactured and marketed.

It is further object of the present invention to provide a new and improved ala-septic pre-cancerous liquid dissolving solution which is of durable and reliable constructions.

An even further object of the present invention is to provide a new and improved ala-septic pre-cancerous liquid dissolving solution which is susceptible of a low cost of manufacture with regard to both materials and labor, and which accordingly is then susceptible of low prices of sale to the consuming public, thereby making such ala-septic pre-cancerous liquid dissolving solution and method economically available to the buying public.

Even still another object of the present invention is to provide an ala-septic pre-cancerous liquid dissolving solution and method for dissolving pre-cancerous tumors and lesions of the skin.

Lastly, it is an object of the present invention to provide a new and improved ala-septic pre-cancerous liquid dissolving solution. Alcohol constitutes a majority of the solution and water, melaleuca alternifolia, amebicidal, acetate, aloe barbadensis, larrea tridentat and benzoic acid constitute a minority of the solution. The minority of the solution optionally includes a corticosteroid and a nutritional supplement.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the descriptive matter in which there is illustrated preferred embodiments of the invention.

DESCRIPTION OF THE PREFERRED EMBODIMENT

The preferred embodiment of the new and improved ala-septic pre-cancerous liquid dissolving solution embodying the principles and concepts of the present invention and generally designated by the reference numeral will be described.

The present invention, the ala-septic pre-cancerous liquid dissolving solution is comprised of a plurality of components. Such components in their broadest context include alcohol as a majority of a solution and a plurality of components as a minority of a solution. Such components are individually configured and correlated with respect to each other so as to attain the desired objective.

First provided is a solution. The solution is a topical medication. The solution is comprised of anti-bacterial, anti-fungal and anti-viral elements. In this manner pre-cancerous tumors and lesions of the skin are dissolved. The specific solution of the preferred embodiment contains 60 percent ethyl alcohol, 11 percent purified water, 10 percent melaleuca alternifolia, 5 percent hydrocortisone, 5 percent iodoquinol, 2 percent tocopheryl acetate, 2 percent aloe barbadensis, 2 percent larrea tridentat, 2 percent oat flour isopropyl palmitate, and 1 percent benzoic acid.

The invention from a broader standpoint is a solution comprising alcohol constituting a majority of the solution and water, melaleuca alternifolia, amebicidal, acetate, aloe barbadensis, larrea tridentat and benzoic acid constituting a minority of the solution minority of the solution.

Optionally, the minority of the solution further includes a corticosteroid. As a further option, the minority of the solution further includes a corticosteroid and a nutritional supplement.

The alcohol is chosen from the class of alcohols which includes ethyl alcohol and denatured ethanol.

The water is chosen from the class of waters. which includes purified water and distilled water.

The amebicidal is chosen from the class of amebicidals which includes iodoquinol and quinoline phosphate.

The acetate is chosen from the class of acetates which includes tocopheryl acetate and alpha-tocopheryl acetate.

The corticosteroid is chosen from the class of corticosteroids which includes hydrocortisone and pramoxine hydrochloride.

The nutritional component is chosen from the class of nutritional components which includes oat flour isopropyl palmitate, cornflower, hybrid safflower oil, kaolin, rye flower and glycerin.

The alcohol constitutes between 57 and 66 percent of the solution. The water constitutes between 7 and 16 percent of the solution. Melaleuca alternifolia constitutes between 8 and 12 percent of the solution. The cortcosteroid and the amebucidal each constitute between 3 and 7 percent of the solution. The acetate, aloe barbadensis, larrea tridentat, nutritional supplement and benzoic acid each constitute between 1 and 3 percent of the solution.

Various alternate embodiments and examples of the solution are as follows:

Example I

Minimum components for ala-septic formulation

Broadest quantitive ranges

Ethyl Alcohol (62-70%)

Purified Water (13-21%)

Melaleuca Alternifolia (8-12%)

Iodoquinol (3-7%)

Tocopheryl Acetate (1-3%)

Example II

Minimum components for ala-septic formulation

Mid-range quantitive ranges

Ethyl Alcohol (64-68%)

Purified Water (15-19%)

Melaleuca Alternifolia (9-11%)

Iodoquinol (4-6%)

Tocopheryl Acetate (1-3%)

Example III

Minimum Components for Ala-septic Formulation

Exact Preferred Quantitive Ranges

Ethyl Alcohol (66%)

Purified Water (17%)

Melaleuca Alternifolia (10%)

Iodoquinol (5%)

Tocopheryl Acetate (2%)

Example IV

Minimum Components for Ala-septic Formulation

Plus One Component

Broadest Quantitive Ranges

Ethyl Alcohol (62-70%)

Purified Water (13-19%)

Melaleuca Alternifolia (8-12%)

Iodoquinol (3-7%)

Tocopheryl Acetate (1-3%)

Benzoic Acid (1-3%)

Example V

Minimum Components for Ala-septic Formulation

Plus One Component

Mid-range Quantitive Ranges

Ethyl Alcohol (64-68%)

Purified Water (14-18%)

Melaleuca Alternifolia (9-11%)

Iodoquinol (4-6%)

Tocopheryl Acetate (1-3%)

Benzoic Acid (1-2%)

Example VI

Minimum Components for Ala-septic Formulation

Plus One Component

Exact Preferred Quantitive Ranges

Ethyl Alcohol (66%)

Purified Water (16%)

Melaleuca Alternifolia (10%)

Iodoquinol (5%)

Tocopheryl Acetate (2%)

Benzoic Acid (1%)

Example VII

Minimum Components for Ala-septic Formulation

Plus Two Components

Broadest Quantitive Ranges

Ethyl Alcohol (62-68%)

Purified Water (11-19%)

Melaleuca Altemifolia (8-12%)

Iodoquinol (3-7%)

Tocopheryl Acetate (1-3%)
Benzoic Acid (1-3%)
Larrea Tridentata (1-3%)

Example VIII

Minimum Components for Ala-septic Formulation
Plus Two Components
Mid-range Quantitive Ranges
Ethyl Alcohol (63-67%)
Purified Water (13-17%)
Melaleuca Alternifolia (9-11%)
Iodoquinol (4-6%)
Tocopheryl Acetate (1-3%)
Benzoic Acid (1-2%)
Larrea Tridentata (1-3%)

Example IX

Minimum Components for Ala-septic Formulation
Plus Two Components
Exact Preferred Quantitive Ranges
Ethyl Alcohol (65%)
Purified Water (15%)
Melaleuca Alternifolia (10%)
Iodoquinol (5%)
Tocopheryl Acetate (2%)
Benzoic Acid (1%)
Larrea Tridentata (2%)

Example X

Minimum Components for Ala-septic Formulation
Plus Three Components
Broadest Quantitive Ranges
Ethyl Alcohol (61-67%)
Purified Water (11-17%)
Melaleuca Alternifolia (8-12%)
Iodoquinol (3-7%)
Tocopheryl Acetate (1-3%)
Benzoic Acid (1-3%)
Larrea Tridentata (1-3%)
Aloe Barbadensis (1-3%)

Example XI

Minimum Components for Ala-septic Formulation
Plus Three Components
Mid-range Quantitive Ranges
Ethyl Alcohol (62-66%)
Purified Water (12-16%)
Melaleuca Alternifolia (9-11%)
Iodoquinol (4-6%)
Tocopheryl Acetate (1-3%)
Benzoic Acid (1-2%)
Larrea Tridentata (1-3%)
Aloe Barbadensis (1-3%)

Example XII

Minimum Components for Ala-septic Formulation
Plus Three Components
Exact Preferred Quantitive Ranges
Ethyl Alcohol (64%)
Purified Water (14%)
Melaleuca Alternifolia (10%)
Iodoquinol (5%)
Tocopheryl Acetate (2%)
Benzoic Acid (1%)
Larrea Tridentate (2%)
Aloe Barbadensis (2%)

Example XIII

Minimum Components for Ala-septic Formulation
Plus Four Components
Broadest Quantitive Ranges
Ethyl Alcohol (58-64%)
Purified Water (8-16%)
Melaleuca Alternifolia (8-12%)
Iodoquinol (3-7%)
Tocopheryl Acetate (1-3%)
Benzoic Acid (1-3%)
Larrea Tridentate (1-3%)
Aloe Barbadensis (1-3%)
Hydrocortisone (3-7%)

Example XIV

Minimum Components for Ala-septic Formulation
Plus Four Components
Mid-range Quantitive Ranges
Ethyl Alcohol (59-63%)
Purified Water (9-15%)
Melaleuca Alternifolia (9-11%)
Iodoquinol (4-6%)
Tocopheryl Acetate (1-3%)

Benzoic Acid (1-2%)

Larrea Tridentata (1-3%)

Aloe Barbadensis (1-3%)

Hydrocortisone (4-6%)

Example XV

Minimum Components for Ala-septic Formulation

Plus Four Components

Exact Preferred Quantitive Ranges

Ethyl Alcohol (61%)

Purified Water (12%)

Melaleuca Alternifolia (10%)

Iodoquinol (5%)

Tocopheryl Acetate (2%)

Benzoic Acid (1%)

Larrea Tridentate (2%)

Aloe Barbadensis (2%)

Hydrocortisone (5%)

Example XVI

Minimum Components for Ala-septic Formulation

Plus Five Components

Broadest Quantitive Ranges

Ethyl Alcohol (57-63%)

Purified Water (7-15%)

Melaleuca Alternifolia (8-12%)

Iodoquinol (3-7%)

Tocopheryl Acetate (1-3%)

Benzoic Acid (1-3%)

Larrea Tridentata (1-3%)

Aloe Barbadensis (1-3%)

Hydrocortisone (3-7%)

Oat Flour Isopropyl Palmitate (1-3%)

Example XVII

Minimum Components for Ala-septic Formulation

Plus Five Components

Mid-range Quantitive Ranges

Ethyl Alcohol (58-62%)

Purified Water (8-14%)

Melaleuca Alternifolia (9-11%)

Iodoquinol (4-6%)

Tocopheryl Acetate (1-3%)

Benzoic Acid (1-2%)

Larrea Tridentata (1-3%)

Aloe Barbadensis (1-3%)

Hydrocortisone (4-6%)

Oat Flour Isopropyl Palmitate (1-3%)

Example XVIII

Minimum Components for Ala-septic Formulation

Plus Five Components

Exact Preferred Quantitive Ranges

Ethyl Alcohol (60%)

Purified Water (11%)

Melaleuca Alternifolia (10%)

Iodoquinol (5%)

Tocopheryl Acetate (2%)

Benzoic Acid (1%)

Larrea Tridentata (2%)

Aloe Barbadensis (2%)

Hydrocortisone (5%)

Oat Flour Isopropyl Palmitate (2%)

The present invention also includes the method of dissolving pre-cancerous tumors and lesions of the skin. Such method includes the steps of first providing an ala-septic pre-cancerous liquid dissolving solution comprises alcohol constituting a majority of the solution and water, melaleuca alternifolia, amebicidal, acetate, aloe barbadensis, larrea tridentat and acid constituting a minority of the solution. The second step is applying the provided solution to each pre-cancerous and malignant lesion at least three times in a 24 hour period.

The components of the solution function together by eliminating bacteria, virus and fungus thereby dissolving the pre-cancerous tumors and lesions. As a result the natural immune system of the body is permitted to completely heal the tumor or lesion.

The solution can also be used to speed the healing processes of the skin when cuts, bruises, and abrasions are present. It helps irritating rashes to heal quickly and painlessly.

The solution of the present invention was primarily developed for the treatment of melanoma. The invention is a topical medication adapted to completely and painlessly dissolve pre-cancerous tumors and lesions on the skin without any scaring thus leaving the derma in its natural color and texture. Application frequency should be at least 3 to 4 times in a 24 hour period, to each pre-cancerous or malignant lesion. Results become obvious in a matter of days.

The solution is part homeopathic and elements within it certainly require a pharmaceutical compounding. This is a unique formula in that it is anti-viral, anti-bacterial and anti-fungal. It functions without pain, burnings, surgery and most important without scaring. This type of medication is unique as it does not require any type of surgery. In additional to all of the above, it also appears to prevent or at the very least delay the formulation of Herbes lesions, a virus affecting some 50 million Americans, at the present time. The solution of the present invention achieves its objective by prevention of replicating the underlying viruses and actually dissolving the tumors and lesions on the surface of the skin, thereby permitting the natural healing process to function As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A pre-melanoma cancerous lesion and a melanoma cancerous lesion dissolving solution, the solution being a topical medication for dissolving pre-cancerous melanoma lesions and melanoma lesions of the skin, the solution comprising, in combination:

60 percent ethyl alcohol;
11 percent purified water;
10 percent melaleuca alternifolia;
5 percent hydrocortisone;
5 percent iodoquinol;
2 percent tocopheryl acetate;
2 percent aloe barbadensis;
2 percent larrea tridentat;
a mixture of 2 percent oat flour and isopropyl palmitate; and
1 percent benzoic acid, the enumerated percentages being by volume.

* * * * *